(12) United States Patent
Dezawa et al.

(10) Patent No.: US 10,034,889 B2
(45) Date of Patent: *Jul. 31, 2018

(54) PHARMACEUTICAL COMPOSITION INCLUDING MIGRATORY FACTOR FOR GUIDING PLURIPOTENT STEM CELLS TO DAMAGE

(71) Applicants: CLIO, INC., Akita (JP); TOHOKU UNIVERSITY, Miyagi (JP); NATIONAL UNIVERSITY CORPORATION NAGOYA UNIVERSITY, Aichi (JP)

(72) Inventors: Mari Dezawa, Miyagi (JP); Yoshinori Fujiyoshi, Aichi (JP); Masanori Yoshida, Akita (JP)

(73) Assignees: CLIO, INC., Akita (JP); TOHOKU UNIVERSITY, Miyagi (JP); NATIONAL UNIVERSITY CORPORATION NAGOYA UNIVERSITY, Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/238,020

(22) Filed: Aug. 16, 2016

(65) Prior Publication Data
US 2016/0354393 A1 Dec. 8, 2016

Related U.S. Application Data

(66) Continuation of application No. 14/711,588, Substitute for application No. PCT/JP2014/055181, filed on Feb. 28, 2014, now Pat. No. 9,446,033.

(30) Foreign Application Priority Data

Mar. 1, 2013 (JP) ................................. 2013-041161

(51) Int. Cl.
| | |
|---|---|
| A61K 31/661 | (2006.01) |
| A61K 31/4164 | (2006.01) |
| A61K 31/417 | (2006.01) |
| A61K 31/4439 | (2006.01) |
| A61K 31/4025 | (2006.01) |
| A61K 31/41 | (2006.01) |
| A61K 31/4178 | (2006.01) |
| A61K 31/4184 | (2006.01) |
| A61K 31/422 | (2006.01) |
| A61K 35/545 | (2015.01) |

(52) U.S. Cl.
CPC ........ *A61K 31/661* (2013.01); *A61K 31/4025* (2013.01); *A61K 31/41* (2013.01); *A61K 31/417* (2013.01); *A61K 31/4164* (2013.01); *A61K 31/4178* (2013.01); *A61K 31/4184* (2013.01); *A61K 31/422* (2013.01); *A61K 31/4439* (2013.01); *A61K 35/545* (2013.01)

(58) Field of Classification Search
CPC .................................................. A61K 31/661

USPC ......................................................... 514/332
See application file for complete search history.

(56) References Cited

U.S. PATENT DOCUMENTS

| | | | |
|---|---|---|---|
| 8,633,211 | B2 | 1/2014 | Taylor |
| 8,642,660 | B2 | 2/2014 | Goldfarb |
| 9,446,033 | B2 | 9/2016 | Dezawa et al. |
| 9,500,642 | B2 | 11/2016 | Blackman et al. |
| 2008/0248032 | A1 | 10/2008 | Saba |
| 2010/0113774 | A1 | 5/2010 | Taylor |
| 2011/0070647 | A1 | 3/2011 | Dezawa et al. |
| 2016/0008340 | A1 | 1/2016 | Dezawa et al. |
| 2017/0304326 | A1 | 10/2017 | Dezawa |

FOREIGN PATENT DOCUMENTS

| | | |
|---|---|---|
| CN | 101361745 A | 2/2009 |
| JP | 2010-520256 A | 6/2010 |
| WO | 2008/107436 A1 | 9/2008 |
| WO | 2011/007900 A1 | 1/2011 |
| WO | 2012/129073 A2 | 9/2012 |

OTHER PUBLICATIONS

Satsu et al. (Bioorganic & Medicinal Chemistry, v. 21, No. 17, 2013, 5373-5382.*
English translation International Search Report corresponding to PCT/JP2014/055181 mailed May 27, 2014 (4 pages).
Bagdanoff, Jeffrey T., et al., "Inhibition of Sphingosine 1-Phosphate Lyase for the Treatment of Rheumatoid Arthritis: Discovery of (E)-1-(4-((1R,2S,3R)-1,2,3,4-Tetrahydroxybutyl)-1H-imidazol-2-yl)ethanone Oxime (LX2931) and 1R2S,3R)-1-(2-(Isoxazol-3-yl)-1H-imidazol-4-yl)butane-1,2,3,4-tetraol (LX2932)," *J. Med. Chem.* (2010) 53(24):8650-8662.
Hong, Cui. et al., "Sphingosine-1-phosphate receptor-2 is protective against lipopolysaccharide-induced, acute lung injury," *The Juzen Medical Society Kanazawa University* (2012) 121(3)106-118.
Ikeda, Hitoshi et al., "Sphingosine 1-phosphate regulates regeneration and fibrosis after liver injury via sphingosine 1-phosphate receptor 2," *Journal of Lipid Research* (2009) 50::556-564.
Park, Sang Won et al., "Inhibition of Sphingosine 1-Phosphate Receptor 2 Protects against Renal Ischemia-Reperfusion Injury," *J. Am Soc. Nephrol.* (2012) 23:266-280.

(Continued)

*Primary Examiner* — Nizal S Chandrakumar
(74) *Attorney, Agent, or Firm* — Kilpatrick Townsend & Stockton LLP (57) ABSTRACT

The purpose of the present invention is to identify a migratory factor that guides pluripotent stem cells (Muse cells) useful in new medical applications to damage, and to provide a pharmaceutical composition that includes the migratory factor for promoting tissue regeneration in regenerative medicine that makes use of Muse cells. In the present invention, a receptor that is specifically expressed in Muse cells rather than non-Muse cells was identified, and it was confirmed that a ligand for this receptor can function as a migratory factor. In the present invention, sphingosine-1-phosphate (S1P) was identified as a migratory factor, and thus, the present invention pertains to a pharmaceutical composition for guiding pluripotent stem cells to damage, the composition including S1P as an active ingredient.

12 Claims, 7 Drawing Sheets

(56) References Cited

OTHER PUBLICATIONS

Pébay, Alice et al., "Stem cell regulation by Lysophospholipids," *Prostaglandins & other Lipid Mediators* (2007) 84:83-97.
Bagdanoff et al., "Inhibition of Sphingosine 1-Phosphate Lyase for the Treatment of Rheumatoid Arthritis: Discovery of (E)-1-(4-((1R,2S,3R)-1,2,3,4-Tetrahydroxybutyl)-1H-imidazol-2-yl)ethanone Oxime (LX2931) and (1R,2S,3R)-1-(2-(Isoxazol-3-yl)-1H-imidazol-4-yl)butane-1,2,3,4-tetraol (LX2932)," J. Med. Chem., 2010, vol. 53, pp. 8650-8662.
Bieberich, "It's a Lipid's World: Bioactive Lipid Metabolism and Signaling in Neural Stem Cell Differentiation", Neurochemical Research; New York, vol. 37, Issue 6, Jun. 2012, pp. 1208-1229.
Mizugishi et al., "Essential Role for Sphingosine Kinases in Neural and Vascular Development", Mol. Cell. Biol., vol. 25, No. 24, Dec. 2005, pp. 11113-11121.
Kimura et al., "Antagonism of Sphingosine 1-Phosphate Receptor-2 Enhances Migration of Neural Progenitor Cells Toward an Area of Brain Infarction," Stroke, Dec. 2008, 39(12), pp. 3411-3417, doi: 10.1161/STROKEAHA.
U.S. Appl. No. 15/642,534, "Final Office Action", dated Apr. 20, 2018, 12 pages.
Li et al., "Homing of Bone Marrow Mesenchymal Stem Cells Mediated by Sphingosine 1-Phosphate Contributes to Liver Fibrosis", Journal of Hepatology, vol. 50, Issue 6, 2009, pp. 1174-1183.
Sallusto et al., "Chemoattractants and Their Receptors in Homeostasis and Inflammation", Current Opinion in Immunology, vol. 16, Issue 6, 2004, pp. 724-731.

\* cited by examiner

Muse cells

(GFP detected by anti-GFP antibody (Alexa 568))

FIG. 9 ial Phase Application of PCT/JP2014/055181, filed
Feb. 28, 2014, which application claims priority to JP
2013-041161, filed Mar. 1, 2013, the disclosures of which
are hereby incorporated by reference for all purposes.

PHARMACEUTICAL COMPOSITION INCLUDING MIGRATORY FACTOR FOR GUIDING PLURIPOTENT STEM CELLS TO DAMAGE

CROSS-REFERENCE TO RELATED APPLICATIONS

This application is a continuation of U.S. patent application Ser. No. 14/771,588, which application is a 371 National Phase Application of PCT/JP2014/055181, filed Feb. 28, 2014, which application claims priority to JP 2013-041161, filed Mar. 1, 2013, the disclosures of which are hereby incorporated by reference for all purposes.

TECHNICAL FIELD

The present invention relates to a pharmaceutical composition that contains a chemotactic factor that guides pluripotent stem cells to a site of tissue damage.

BACKGROUND ART

Recently, attention has been focused on biological cells capable of contributing to tissue regeneration. Although known examples of cells obtained from adults that have differentiation ability include mesenchymal stem cells (MSC) that have the ability to differentiate into bone, cartilage, adipocytes, neurons or skeletal muscle and the like (Non-Patent Documents 1 and 2), these consist of cell groups containing various cells, the actual state of their ability to differentiate is not understood, and there have been considerable fluctuations in therapeutic effects. In addition, although iPS cells (Patent Document 1) have been reported to be adult-derived pluripotent stem cells, in addition to the establishment of iPS cells requiring an extremely complex procedure involving the introduction of specific genes into mesenchymal cells in the form of a skin fibroblast fraction and the introduction of specific compounds into somatic cells, since iPS cells have a high tumorigenic potential, extremely high hurdles must be overcome for their clinical application.

It has been determined from research by M. Dezawa, one of the inventors of the present invention, that multilineage-differentiating stress enduring cells (Muse cells) expressing surface antigen in the form of stage-specific embryonic antigen-3 (SSEA-3), which are present in mesenchymal cell fractions and can be obtained without going through an induction procedure, are responsible for the pluripotency possessed by mesenchymal cell fractions, and that they have the potential for application to disease treatment aimed at tissue regeneration (Patent Document 2, Non-Patent Document 3, Non-Patent Document 4). In addition, pluripotent stem cells (Muse cells) have been determined to be present in mesenchymal tissue of the body, accumulate at the site of a tissue damage when body tissue has been damaged and be responsible for tissue regeneration (Patent Document 2, Non-Patent Document 3). However, not only has the mechanism by which Muse cells are guided to damaged tissue not been elucidated, but the chemotactic factor that guides Muse cells to the damaged site has also not been identified.

PRIOR ART DOCUMENTS

Patent Documents

[Patent Document 1] Japanese Patent No. 4183742
[Patent Document 2] International Publication No. WO 2011/007900

Non-Patent Documents

[Non-Patent Document 1] Dezawa, M., et al., J. Clin. Invest., Vol. 113, p. 1701-1710 (2004)
[Non-Patent Document 2] Dezawa, M., et al., Science, Vol. 309, p. 314-317 (2005)
[Non-Patent Document 3] Kuroda, Y., et al., Proc. Natl. Acad. Sci. USA, Vol. 107, p. 8639-8643 (2010)
[Non-Patent Document 4] Wakao, S., et al., Proc. Natl. Acad. Sci. USA, Vol. 108, p. 9875-9880 (2011)

DISCLOSURE OF THE INVENTION

Problems to be Solved by the Invention

An object of the present invention is to provide a medical application using pluripotent stem cells (Muse cells) in the field of regenerative medicine, and to enhance the chemotactic activity of Muse cells and identify a chemotactic factor for allowing Muse cells to effectively accumulate at a damaged site together with providing a pharmaceutical composition containing that chemotactic factor.

Means for Solving the Problems

The inventors of the present invention succeeded in identifying chemotactic factors that guide Muse cells to a damage site by utilizing a proteomic analysis, and found that one of those chemotactic factors in the form of sphingosine-1-phosphate (S1P) enhances the chemotactic activity of Muse cells and is involved in their accumulation at a damage site, thereby leading to completion of the present invention. Enhancement of chemotactic activity includes initiating migration of Muse cells present in mesenchymal tissue towards a damage site.

Namely, the present invention is as indicated below.

[1] A pharmaceutical composition for activating migration of pluripotent stem cells, comprising: as an active ingredient thereof a compound that activates sphingosine-1-phosphate receptor 2.

[2] The pharmaceutical composition described in [1] above, wherein the compound that activates sphingosine-1-phosphate receptor 2 is an agonist of sphingosine-1-phosphate receptor 2.

[3] The pharmaceutical composition described in [2] above, wherein the agonist of sphingosine-1-phosphate receptor 2 is sphingosine-1-phosphate or a derivative thereof.

[4] The pharmaceutical composition described in [2] above, wherein the agonist of sphingosine-1-phosphate receptor 2 is selected from the group consisting of 1-(2-(1-benzyl-2,5-dimethyl-1H-pyrrol-3-yl)-2-oxoethyl)-5-(trifluoromethyl) pyridin-2(1H)-one, 1-(2-(1-benzyl-2,5-dimethyl-1H-pyrrol-3-yl)-2-oxoethyl)pyrrolidine-2,5-dione, 1-(2-(1-benzyl-2,5-dimethyl-1H-pyrrol-3-yl)-2-oxoethyl)-3-methylimidazolindine-2,4,5-trione, 1-(1-benzyl-2,5-dimethyl-1H-pyrrol-3-yl)-2-((1-methyl-1H-tetrazol-5-yl)thio) ethanone, and (S)-1-(2-(1-benzyl-2,5-dimethyl-1H-pyrrol-3-yl)-2-oxoethyl-2',3'-dihydrospiro[imidazolidine-4,1'-indene]-2,5-dione.

[5] The pharmaceutical composition described in [1] above, wherein the compound that activates sphingosine-1-phosphate receptor 2 is a sphingosine-1-phosphate lyase inhibitor.

[6] The pharmaceutical composition described in [5] above, wherein the sphinigosine-1-phosphate lyase inhibitor is selected from the group consisting of (E)-1-(4-((1R,2S, 3R)-1,2,3,4-tetrahydroxybutyl)-1H-imidazol-2-yl)ethanone oxime, (1R,2S,3R)-1-(2-isoxazol-3-yl)-1H-imidazol-4-yl) butane-1,2,3,4-tetraol, and 1-(5-((1R,2S,3R)-1,2,3,4-tetrahydroxybutyl)-1H-imidazol-2-yl)ethanone.

[7] The pharmaceutical composition described in [1] to [6] above, wherein activation of migration is guidance to a damaged site in the body.

[8] The pharmaceutical composition described in [1] to [7] above, wherein the pluripotent stem cells are SSEA3-positive.

[9] The pharmaceutical composition described in [1] to [8] above, wherein the pluripotent stem cells are CD105-positive.

[10] The pharmaceutical composition described in [1] to [9] above, wherein the pluripotent stem cells are CD117-negative and CD146-negative.

[11] The pharmaceutical composition described in [1] to [10] above, wherein the pluripotent stem cells are CD117-negative, CD146-negative, NG2-negative, CD34-negative, vWF-negative and CD271-negative.

[12] The pharmaceutical composition described in [1] to [11] above, wherein the pluripotent stem cells are CD34-negative, CD117-negative, CD146-negative, CD271-negative, NG2-negative, vWF-negative, Sox10-negative, Snail-negative, Slug-negative, Tyrp1-negative and Dct-negative.

[13] The pharmaceutical composition described in [1] to [12] above, wherein the pluripotent stem cells are pluripotent stem cells having all of the following properties:
  (i) low or absent telomerase activity;
  (ii) ability to differentiate into cells of any of the three germ layers;
  (iii) absence of demonstration of neoplastic proliferation; and,
  (iv) presence of self-renewal ability.

Effects of the Invention

According to the present invention, a pharmaceutical composition is provided that comprises a chemotactic factor that enhances the chemotactic activity of Muse cells and guides Muse cells to the site of a damage during tissue regeneration by Muse cells.

MODE FOR CARRYING OUT THE INVENTION

The present invention relates to a composition comprising a chemotactic factor that guides pluripotent stem cells to a damaged site, and to the utilization thereof. The following provides a detailed explanation of the present invention.
1. Pluripotent Stem Cells (Muse Cells)

The existence of the pluripotent stem cells which are guided to the damaged site by the chemotactic factor of the present invention was discovered by M. Dezawa, one of the applicants of the present invention, and the cells were named "multilineage-differentiating stress enduring (Muse) cells". Muse cells can be obtained from bone marrow aspirates or skin tissue such as dermal connective tissue, and are sporadically present in the connective tissue of various organs. In addition, these cells have both the properties of pluripotent stem cells and mesenchymal stem cells, and are identified as being double-positive for each of the cell surface markers of "stage-specific embryonic antigen-3 (SSEA-3)" and "CD105". Thus, Muse cells or cell populations containing Muse cells can be isolated from body tissue by using these antigen markers as indicators. Details regarding methods used to isolate and identify Muse cells as well as their characteristics are disclosed in International Publication No. WO 2011/007900. In addition, as has been reported by Wakao, et al. (2011, previously cited), in the case of using a cell culture obtained by culturing mesenchymal cells present in bone marrow, skin and the like and using the cells as the parent population of Muse cells, all cells positive for SSEA-3 are known to be positive for CD105. Thus, in the pharmaceutical composition of the present invention, in the case of isolating Muse cells from biological mesenchymal tissue or cultured mesenchymal cells, Muse cells can be purified and used simply by using SSEA-3 as an antigen marker. Furthermore, in the present description, pluripotent stem cells (Muse cells) that have been isolated from biological mesenchymal tissue or cultured mesenchymal cells by using SSEA-3 as an antigen marker, or a cell population containing Muse cells, may simply be described as "SSEA-3-positive cells". Further, in the present description, "non-Muse cells" refers to cells that are contained in the biological mesenchymal tissue or cultured mesenchymal cells, and that are not "SSEA-3-positive cells".

Simply speaking, Muse cells or cell populations containing Muse cells can be isolated from biological tissue (such as mesenchymal tissue) using antibody to the cell surface marker SSEA-3 alone or using both an antibody to SSEA-3 and an antibody to CD105. Here, "biological tissue" refers to the biological tissue of a mammal. In the present invention, although an embryo in a development stage prior to a fertilized egg or blastula stage is not included in biological tissue, an embryo in a development stage in or after the fetus or blastula stage, including the blastula, is included. Examples of mammals include, but are not limited to, primates such as humans or monkeys, rodents such as mice, rats, rabbits or guinea pigs as well as cats, dogs, sheep, pigs, cows, horses, donkeys, goats and ferrets. The Muse cells used in the cell preparation of the present invention are clearly distinguished from embryonic stem (ES) cells and embryonic germ (EG) cells in that they are derived from biological tissue. In addition, "mesenchymal tissue" refers to tissue of bone, synovial membrane, fat, blood, bone marrow, skeletal muscle, dermis, ligaments, tendons, pulp, umbilical and the like, as well as connective tissue present in various organs. For example, Muse cells can be obtained from bone marrow and skin. For example, Muse cells are preferably used that have been isolated from mesenchymal tissue collected from the living body. In addition, Muse cells may also be isolated from cultured mesenchymal cells using the aforementioned isolation means.

As has been described above, although Muse cells or cell populations containing Muse cells can be isolated from biological tissue by using their property of being SSEA-3-positive or SSEA and CD105 double-positive, human adult skin is known to contain various types of stem cells and precursor cells. However, Muse cells are not the same as these cells. Examples of such stem cells and precursor cells include skin-derived precursor (SKP) cells, neural crest stem cells (NCSC), melanoblasts (MB), perivascular cells (PC), endothelial precursor (EP) cells and adipose-derived stem cells (ADSC). Muse cells can be isolated from these cells by using "non-expression" of a unique marker as an indicator of these cells. More specifically, Muse cells can be isolated by using non-expression of at least one of 11 markers, such as 1, 2, 3, 4, 5, 6, 7, 8, 9, 10 or 11 markers, selected from the group consisting of CD34 (marker for EP and ADSC), CD117 (c-kit) (MB marker), CD146 (PC and ADSC marker), CD271 (NGFR) (NCSC marker), NG2 (PC marker), vWF factor (von Willebrand factor) (EP marker), Sox10 (NCSC marker), Snail (SKP marker), Slug (SKP marker), Tyrp1 (MB marker) and Dct (MB marker). For example, although not limited thereto, Muse cells can be isolated by using non-expression of CD117 and CD146 as an indicator, can be isolated using non-expression of CD117, CD146, NG2, CD34, vWF and CD271 as an indicator, and can be isolated by using non-expression of the aforementioned 11 markers as an indicator.

In addition, Muse cells having the aforementioned characteristics used in the cell preparation of the present invention may have at least one property selected from the group consisting of:
 (i) low or absent telomerase activity;
 (ii) ability to differentiate into any of the three germ layers;
 (iii) absence of demonstration of neoplastic proliferation; and,
 (iv) self-renewal ability.

In one aspect of the present invention, the Muse cells used in the cell preparation of the present invention have all of the aforementioned properties. Here, with respect to the aforementioned (i), "low or absent telomerase activity" refers to telomerase activity being low or being unable to be detected in the case of having detected telomerase activity using, for example, the Trapeze XL Telomerase Detection Kit (Millipore Corp.). "Low" telomerase activity refers to having telomerase activity roughly equal to that of human fibroblasts, for example, or having telomerase activity that is $1/5$ or less and preferably $1/10$ or less in comparison with Hela cells. With respect to the aforementioned (ii), Muse cells have the ability to differentiate into the three germ layers (endoderm, mesoderm and ectoderm) in vitro and in vivo, and by inducing to differentiate by culturing in vitro, for example, can differentiate into hepatocytes, neurocytes, skeletal muscle cells, smooth muscle cells, osteocytes, adipocytes and the like. In addition, Muse cells may also demonstrate the ability to differentiate into the three germ layers in the case of transplanting in vivo into testes, for example. Moreover, Muse cells also have the ability to migrate, graft and differentiate into a damaged organ (such as the heart, skin, spinal cord, liver or muscle) by being transplanted into the body by intravenous injection. With respect to the aforementioned (iii), although Muse cells proliferate at a growth rate of about 1.3 days in a suspension culture, they also have the property of discontinuing proliferation for about 10 days, and in the case of having been transplanted into testes, have the property of not becoming malignant for at least six months. In addition, with respect to the aforementioned (iv), Muse cells have self-renewal (self-replication) ability. Here, "self-renewal" refers to culturing cells contained in an embryoid body-like cell mass obtained by suspension culturing single Muse cells and allowing them to reform an embryoid body-like cell mass. Self-renewal may be carried out for one cycle or repeated for a plurality of cycles.

2. Identification of Protein Specifically Expressed in Muse Cells

Although Muse cells have previously been known to converge on damaged sites when administered to an adult while non-Muse cells do not, the chemotactic factor that guides the Muse cells to a damaged site is not known. Therefore, in the case of hypothesizing the existence of a chemotactic factor that guides Muse cells to a damaged site, by identifying a protein (particularly a receptor) that is specifically expressed in Muse cells but not expressed in non-Muse cells, there is thought to be a high possibility that the corresponding ligand and the like is a chemotactic factor.

In general, proteomic analysis is known to be useful as a technique for identifying unknown factors. This analysis is an analytical technique for conducting research for the purpose of determining the correlation between a protein extracted from cells or tissue and a gene that encodes it by analyzing the biochemical and physicochemical properties of the aforementioned protein and using genetic information determined from a genome analysis, and further determining the functions of the translation products of all genes while utilizing genome sequence information.

In a proteomic analysis, an example of a technique that is currently used frequently is peptide mass fingerprinting (PMF). In PMF, after isolating a protein by two-dimensional electrophoresis and the like and digesting that protein into peptides with a digestive enzyme such as trypsin, the mass spectrum of the peptide mixture (peptide mass fingerprint) is acquired using a mass spectrometer, and by searching a genome database for this spectrum and the theoretical mass spectrum calculated from an amino acid sequence corresponding to the DNA base sequence, that protein and the gene encoding that protein can be identified.

According to the present invention, a proteomic analysis developed by a group led by Professor Toshiaki Isobe of the Tokyo Metropolitan University can be used for the purpose of identifying receptors for chemotactic factors of Muse cells. More specifically, proteins (mixtures) are extracted from two cell groups to be compared (Muse cell group and non-Muse cell group), and these mixtures are isolated by electrophoresis based on differences in molecular weight. The isolated proteins are distinguished as respective bands in a gel. Next, each band is cut out from the gel and the mass thereof is measured by LC-MS analysis. Moreover, proteins are searched for automatically and selected from a database by using these mass values, thereby making it possible to identify proteins that differ between the two cell groups (see, for example, Taoka, M., et al., "Protein Analysis Model— The Definitive Version!", Isobe, T. and Takahashi N., ed., pp. 92-100, Yodosha Co., Ltd., 2004). Furthermore, although there are no limitations on the aforementioned database, a previously publicly disclosed protein database in the form of "Swiss Prot" can be used. The inventors of the present invention identified proteins specifically expressed in Muse cells by comparing with non-Muse cells using the aforementioned proteomic analysis (data not shown). As will be subsequently described, among these identified proteins, sphingosine-1-phosphate receptor 2 (which may be abbreviated as "S1PR2"), for example, was determined to be a protein that is specifically expressed in Muse cells but not expressed in non-Muse cells (Example 2).

3. Identification and Confirmation of Chemotactic Factor

Figure 2:
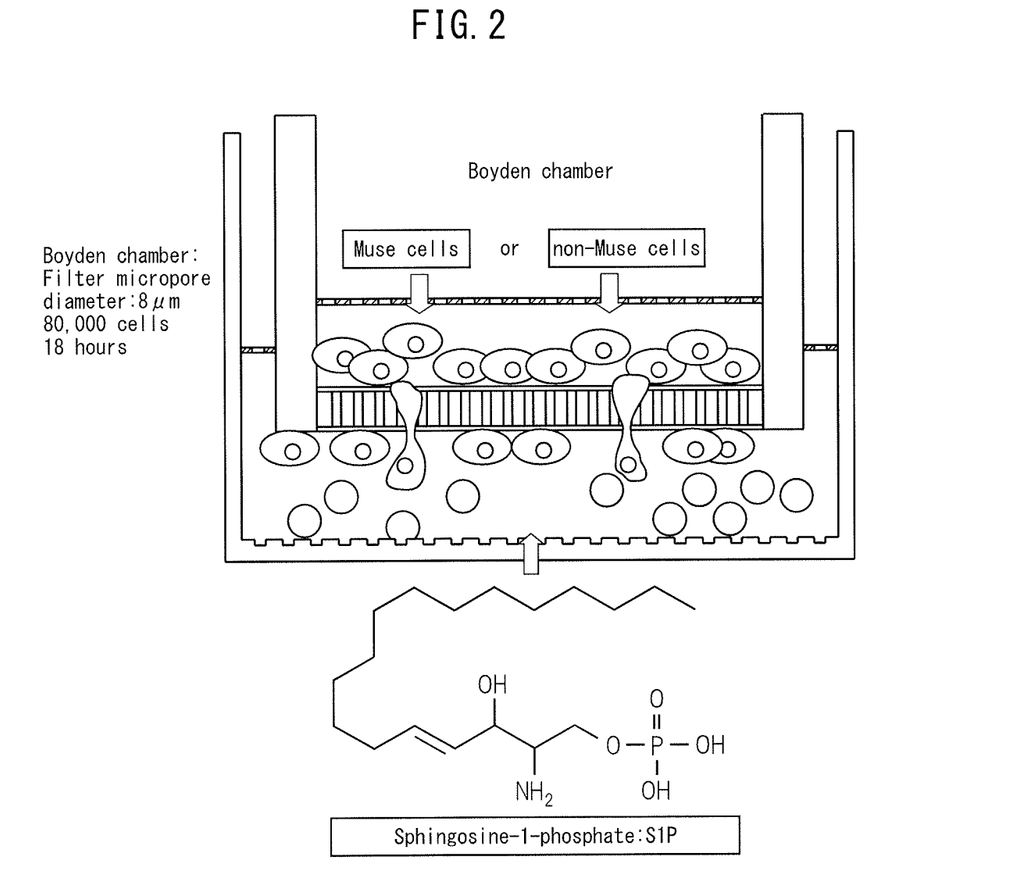
FIG. 2 is a drawing schematically showing a Boyden chamber used to measure migration of Muse cells and cell migration induced by a chemotactic factor. The Boyden chamber has an insert having a micropore diameter of 8 µm inside. A culture broth containing Muse cells or non-Muse cells is added above the insert, a culture broth containing chemotactic factor is added below the insert, and the number of cells that have passed through the insert after 18 hours is counted.

Chemotactic factors of Muse cells can be identified by selecting proteins specifically expressed in Muse cells identified in the manner described above that are able to serve as receptors of chemotactic factors, and then examining whether or not ligands for these receptors can be chemotactic factors. In general, although there are no particular limitations on the method used to measure cell migration, methods such as the Boyden chamber method or cell kinetics analysis technology can be used in in vitro experimental systems. Simply speaking, the Boyden chamber method is a method that is effective for quantifying chemotactic activity, and consists of providing an insert as a separate compartment in a Boyden chamber and installing a filter having a large number of uniform size (for example, about 8 μm) micropores on the bottom of this insert. By adding a culture broth containing cells above the filter and adding a culture broth containing a chemotactic factor below the insert, the cells migrate downward by passing through the filter along the concentration gradient of the chemotactic factor generated in the micropores of the filter, and this migration is used to quantify chemotactic activity (FIG. 2) (see, for example, Boyden, S., J. Exp. Med., Vol. 115, p. 453-466 (1962)). In this manner, the degree of chemotaxis can be measured quantitatively by counting the number of cells that pass through the filter. In the present invention, after adding a candidate substance of a chemotactic factor below an insert and adding Muse cells above the insert, the number of Muse cells that migrated through the insert are counted, thereby making it possible to evaluate whether or not the added candidate substance is able to act as a chemotactic factor.

On the other hand, cell kinetics analysis technology refers to a system enabling measurement of concentration gradient-dependent chemotactic activity of cells in the horizontal direction by forming a constant chemotactic factor concentration gradient on a glass substrate using a silicon wafer chip fabricated using the latest microfabrication technology. Directivity (such as the degree to which Muse cells proceed towards the high concentration side of a chemotactic factor in a certain direction) can be quantified by analyzing images obtained using this system on a real-time basis. As will be subsequently described in detail, in the case of using sphingosine-1-phosphate (S1P) as a single candidate substance, Muse cells were observed to demonstrate remarkable chemotactic activity in experimental systems employing the Boyden chamber method and cell kinetics analysis technology (Example 2).

In addition, in in vivo experimental systems, chemotactic factors can be identified by using a system in which mice, for example, are used for the experimental model. More specifically, a gel (such as hydrogel) impregnated with a chemotactic factor is transplanted into the tissue of immunodeficient mice that do not reject human cells, and by subsequently administering human Muse cells labeled with GFP into a tail vein, the chemotactic factor can be identified by histochemically observing whether or not the Muse cells are able to accumulate in the transplanted gel containing the chemotactic factor. As indicated in Example 2 to be subsequently described, GFP-positive Muse cells were determined to accumulate dependent on the concentration of S1P.

4. Utilization of Chemotactic Factor

The present invention provides a pharmaceutical composition that comprises as an active ingredient thereof a chemotactic factor that enhances chemotactic activity of Muse cells and guides Muse cells to a damaged site. A "chemotactic factor" used in the pharmaceutical composition of the present invention refers to, for example, a substance that causes cells to migrate towards that chemotactic factor as a result of binding to a receptor expressed on the surface of Muse cells and activating a signal transduction system involved in cell migration by means of that binding. In addition, when used in the present invention, the term "damaged site" refers to a specific site in various organs or tissues in the body for which function has been lost due to degeneration or elimination with various types of cells and tissues caused by trauma, inflammation, disease, ischemia, necrosis, tumorigenesis or aging and the like. According to the present invention, in order to allow Muse cells to accumulate at a damaged site, a chemotactic factor may be used as a pharmaceutical composition obtained by incorporating a pharmacologically acceptable carrier and/or diluent, or the chemotactic factor may be used alone. Here, there are no particular limitations on the chemotactic factor contained in the pharmaceutical composition of the present invention provided it is a substance that has the ability to guide Muse cells to a damaged site (examples of which include proteins, peptides, lipids and chemical compounds). More preferably, the chemotactic factor is an agonist of sphingosine-1-phosphate (S1P), a sphingosine-1-phosphate derivative or a sphingosine-1-phosphate receptor. Here, "sphingosine-1- phosphate (S1P)" refers to a metabolic product of a sphingolipid composing the cell membrane that has the formula indicated below.

[Chemical Formula 1]

S1P is known to be a physiologically active substance that induces migration by being released after being cleaved from the cell membrane by certain types of enzymes and then binding to a G protein-coupled receptor expressed on the cell membrane. In addition, a G protein-coupled receptor in the form of S1P receptor is known to be a receptor for S1P, and five types have previously been determined to exist, consisting of S1PR1 to S1PR5. Here, when an investigation was made of the expression of S1P receptor in Muse cells and non-Muse cells, although S1PR1 was determined to be expressed in both cells, SP1R2 was determined by the inventors of the present invention to be expressed in Muse cells (data not shown).

According to the present invention, the chemotactic factor used in the pharmaceutical composition of the present invention is not limited to S1P, but can also be an S1P derivative thereof, provided it is a substance that enhances the chemotactic activity of Muse cells. Although there are no particular limitations thereon, examples of S1P derivatives include sphingosyl choline, galactosyl sphingosine (psychosine), glucosyl sphingosine (glucopsychosine), sulfogalactosyl sphingosine (lysosulfatide), N,N-dimethylsphingosine-1-phosphate, N,N,N-trimethylsphingosine-1-phosphate, ceramide-1-phosphate, dihydrosphinogisine-1-phosphate, phytosphingosine-1-phosphate, dehydrophytosphingosine-1-phosphate and salts thereof. In addition, according to the present invention, an agonist for S1PR2 can be used for the chemotactic factor used in the pharmaceutical composition of the present invention. Examples of such agonists include an agonist having the following structure:

[Chemical Formula 2]

representing 1-(2-(1-benzyl-2,5-dimethyl-1H-pyrrol-3-yl)-2-oxoethyl)-5-(trifluoromethyl)pyridin-2(1H)-one (refer to, for example, Park, S. W., et al., J. Am. Soc. Nephrol., Vol. 23, p. 266-280 (2012)), an agonist having the following structure:

[Chemical Formula 3]

representing 1-(2-(1-benzyl-2,5-dimethyl-1H-pyrrol-3-yl)-2-oxoethyl)pyrrolidine-2,5-dione, an agonist having the following structure:

[Chemical Formula 4]

representing 1-(2-(1-benzyl-2,5-dimethyl-1H-pyrrol-3-yl)-2-oxoethyl)-3-methylimidazolindine-2,4,5-trione, an agonist having the following structure:

[Chemical Formula 5]

representing 1-(1-benzyl-2,5-dimethyl-1H-pyrrol-3-yl)-2-((1-methyl-1H-tetrazol-5-yl)thio)ethanone, and an agonist having the following structure:

[Chemical Formula 6]

representing (S)-1-(2-(1-benzyl-2,5-dimethyl-1H-pyrrol-3-yl)-2-oxoethyl-2',3'-dihydrospiro[imidazolidine-4,1'-indene]-2,5-dione.

In addition, although S1P is desphosphorylated in the body by sphingosine-1-phosphate lyase present in endoplasmic reticulum causing it to be broken down into trans-2-hexadecenal and ethanolamine phosphate, this dephosphorylation reaction is known to normally be in a state of equilibrium with a reaction that adds phosphoric acid to trans-2-hexadecenal. Therefore, a substance that inhibits S1P lyase, which is responsible for dephosphorylation, can also be used in the pharmaceutical composition of the present invention in order to enhance S1P concentration. Examples of such substances that inhibit S1P lyase include a substance having the following structure:

[Chemical Formula 7]

representing (E)-1-(4-((1R,2S,3R)-1,2,3,4-tetrahydroxybutyl)-1H-imidazol-2-yl)ethanone oxime (see, for example, Bagdanoff, J. T., et al., J. Med. Chem., Vol. 53, p. 8650-8662 (2010)), a substance having the following structure:

[Chemical Formula 8]

Structure:

representing (1R,2S,3R)-1-(2-isoxazol-3-yl)-1H-imidazol-4-yl)butane-1,2,3,4-tetraol (Bagdanoff, et al., ibid), and a substance having the following structure:

[Chemical Formula 9]

Structure:

representing 1-(5-((1R,2S,3R)-1,2,3,4-tetrahydroxybutyl)-1H-imidazol-2-yl)ethanone (see, for example, Cayman Chemical Item Number 13222, Cayman Chemical Co., Michigan, USA).

In the case of using the pharmaceutical composition comprising a chemotactic factor of the present invention for treatment for the purpose tissue regeneration, there are no particular limitations on the administration route and can be suitably selected corresponding to the purpose of treatment. For example, although the pharmaceutical composition of the present invention may be any of an injection preparation, oral preparation, suppository or inhalant and the like, in the case of aiming to accumulate Muse cells at a damaged site, it is more preferable to administer the chemotactic factor of pharmaceutical composition of the present invention directly into the damaged site. On the other hand, in the case of modifying the pharmaceutical composition of the present invention so as to be delivered to a damaged site, administration of the pharmaceutical composition is not limited to direct injection to the damaged site, but rather the pharmaceutical composition can also be administered intravenously. In addition, the pharmaceutical composition can also be administered systemically such as by intravenous administration for the purpose of initiating migration of Muse cells present in mesenchymal tissue in the body. Furthermore, pharmaceutical compositions suitable for these administration forms can be produced using known preparation methods.

In the case of preparing an injection preparation, a local injection preparation can be produced using ordinary methods by adding a pH adjuster, buffer, stabilizer, tonicity agent or local anesthetic and the like to the chemotactic factor. Examples of pH adjusters and buffers include sodium citrate, sodium acetate and sodium phosphate. Examples of stabilizers include sodium pyrosulfite, EDTA (sodium edetate), thioglycolic acid and thiolactic acid. Examples of local anesthetics include procaine hydrochloride and lidocaine hydrochloride. Examples of tonicity agents include sodium chloride and glucose.

In addition, in the case of directly injecting the pharmaceutical composition or chemotactic factor of the present invention into a damaged site, a sheet may be used in which the pharmaceutical composition or chemotactic factor of the present invention is contained in a carrier such as a biodegradable hydrogel that contains ingredients of the aforementioned injection preparations. Examples of biodegradable hydrogel that can be used include, but are not limited to, gels having collagen, fibronectin, gelatin or agarose as a main component thereof. Moreover, in addition to being injected directly into a damaged site, the pharmaceutical composition or chemotactic factor of the present invention can be coated onto the inner diameter of a stent used for the purpose of vasodilation when an infarction and the like has occurred. In addition, a component (such as a growth factor or cytokine) that enhances the viability of accumulated Muse cells may also be incorporated for the purpose of supporting tissue regeneration by Muse cells.

The concentration of chemotactic factor contained in the pharmaceutical composition of the present invention can be suitably adjusted according to the degree of damage at the damaged site and the type of chemotactic factor. Although there are no particular limitations thereon, the effective chemotactic factor concentration for guiding Muse cells is, for example, 1 nM to 100 µM. In addition, in the case of injecting or administering chemotactic factor in the form of a pharmaceutical composition, the injected amount or administered amount of the pharmaceutical composition, administration form, number of administrations and administration interval and the like can be suitably selected in consideration of the chemotactic factor concentration or degree of damage as previously described.

Although the following provides a more detailed explanation of the present invention through examples thereof, the present invention is not limited in any way by these examples.

EXAMPLES

Example 1: Selection of Chemotactic Factor Candidate Substances by Proteomic Analysis A proteomic analysis method developed by a group led by Professor Isobe of the Tokyo Metropolitan University (see Taoka, et al. (2004), ibid) was used to select candidate substances of chemotactic factors that guide Muse cells to a damaged site. This method is a method for identifying large numbers of proteins contained in a sample by analyzing a complex peptide mixture obtained by digesting a protein mixture with protease, and is also referred to as the "shotgun method". An automated system for carrying out this method is composed of an integrated LC system combining an ion exchange LC, separating reverse phase LC and desalination system, a hybrid mass spectrometer and a data analysis system. The integrated LC system is characterized in particular by the combining of two types of LC having different separation modes (ion exchange mode and reverse phase mode), and since the resolution of the overall system is obtained as the product of the resolution of each separation method, an extremely large number of proteins or peptides can be separated. Next, a biological sample is separated at high resolution dependent on mass, and by using MS that provides mass data, proteins or peptides can be identified by subsequently searching a database containing sequence information. For example, 2,000 to 3,000 types of peptides derived from roughly 1,000 types of proteins can be identified by acquiring approximately 10,000 to 15,000 MS/MS spectra in a single round of analysis from an extremely complex mixture of peptides obtained by digesting a crude cell or tissue extract with trypsin. In the present example, use of the automated system developed by Isobe et al. as previously described made it possible to identify proteins specifically expressed in Muse cells in comparison with non-Muse cells.

Example 2: Identification of Chemotactic Factors (1) Preparation of Human Muse Cells Preparation of human Muse cells was carried out in accordance with the method described in International Publication No. WO 2011/007900. More specifically, adhesive mesenchymal cells were cultured from human bone marrow aspirate followed by allowing the cells to proliferate and introducing lentivirus-GFP into the cells. A cell population containing GFP-labeled Muse cells or Muse cells was separated by FACS as cells double-positive for GFP and SSEA-3. In addition, non-Muse cells constituted a GFP-positive cell group of the aforementioned mesenchymal cells that is negative for SSEA-3, and these cells were used as a control. Subsequently, the cells were adjusted to prescribed concentrations using phosphate-buffered physiological saline or culture broth and then used in the Boyden chamber method and cell kinetics analysis technology described below. Furthermore, in the case of using cells obtained by culturing mesenchymal cells such as bone marrow mesenchymal cells as a parent population of Muse cells, all SSEA-3-positive cells have been determined to be CD105-positive cells as reported in Wakao, et al. (2011, ibid).

Figure 1:
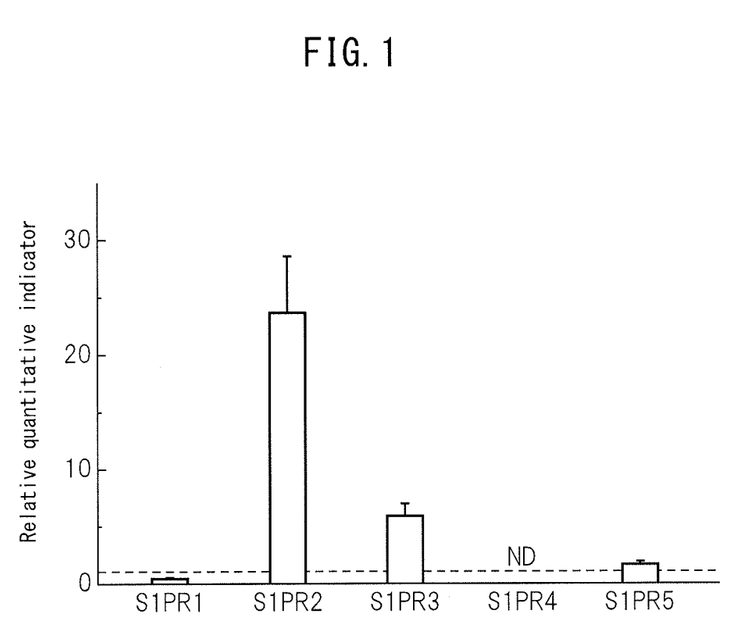
FIG. 1 is a graph indicating the results of measuring expression levels of various types of sphingosine-1-phosphate receptors (S1PR) in Muse cells as relative values based on expression levels in normal human dermal fibroblasts (NHDF) using real-time PCR (quantitative PCR).

One of the chemotactic factor candidates obtained in the aforementioned Example 1 in the form of sphingosine-1-phosphate receptor 2 (S1PR2) was suggested to have the possibility of being specifically expressed in Muse cells. Therefore, when expression of receptor for S1P in Muse cells and non-Muse cells was attempted to be investigated by proteomic analysis, S1PR2 was determined to be only expressed in Muse cells (data not shown). In addition, S1PR1 was expressed in both Muse cells and non-Muse cells (data not shown). Moreover, since S1PR is known to have five types consisting of S1PR1, S1PR2, S1PR3, S1PR4 and S1PR5 based on differences in expression sites, amino acid sequences and base sequences thereof, a comparison was made of the presence or absence of their expression and differences in expression levels thereof in Muse cells by real-time PCR (quantitative PCR) (FIG. 1). In consideration of the above results, S1PR2 was suggested to be specifically expressed in Muse cells. Therefore, S1P that binds to S1PR2 was confirmed to be one of the chemotactic factors specific to Muse cells using the experimental systems described below.

(2) Boyden Chamber Method

The Boyden chamber method was used to quantitatively measure migration of Muse cells induced by chemotactic factor. The QCM Chemotaxis Cell Migration Assay Kit (QCM 24-Well Colorimetric Cell Migration Assay), commercially available from Millipore Corp., was used for the Boyden chamber. This Boyden chamber contains an insert having a filter on the bottom thereof that has uniform 8 μm micropores therein. Culture broth containing Muse cells or non-Muse cells is added above the filter on the insert, culture broth containing a chemotactic factor is added below the insert, and the number of cells that have passed through the micropores of the filter is counted after incubating for 18 hours (see FIG. 2). The use of this method makes it possible to identify chemotactic factors for Muse cells by testing each of the chemotactic factor candidates obtained in Example 1.

Figure 3:
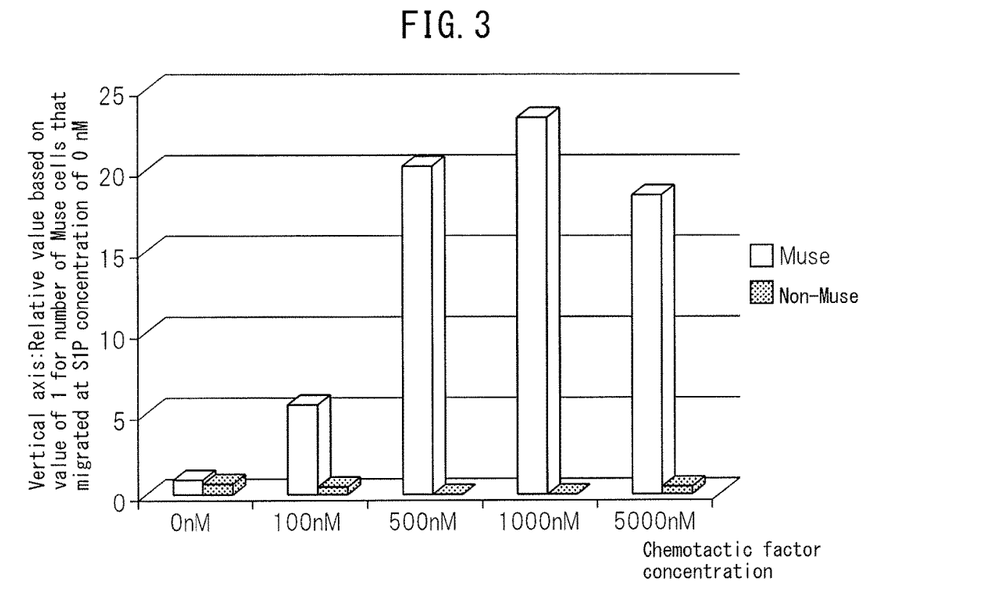
FIG. 3 is a graph indicating a relative evaluation of the numbers of migrated cells measured using a Boyden chamber. In the graph, different concentrations of chemotactic factor are plotted on the horizontal axis, and relative values are plotted on the vertical axis based on a value of 1 for the number of Muse cells that were induced to migrate by the chemotactic factor (0 nM).

More specifically, Muse cells or non-Muse cells were plated at a concentration of $1 \times 10^5$ cells/well onto the filter, and a culture broth containing a prescribed concentration of S1P (0 nM, 100 nM, 500 nM, 1000 nM or 5000 nM) was added below the insert. After incubating the cells for 18 hours, the number of cells that passed through the micropores of the filter was counted. The results are shown in FIG. 3. In the graph, the different concentrations of S1P are plotted on the horizontal axis, while the relative values of the number of cells for each concentration based on a value of 1 for the number of Muse cells that migrated at an S1P concentration of 0 μm are plotted on the vertical axis. As is also clear from FIG. 3, in the system in which Muse cells were added, since the number of cells that migrated increased dependent on the concentration of S1P, S1P was suggested to function as a chemotactic factor with respect to Muse cells. On the other hand, since non-Muse cells did not demonstrate chemotactic activity with respect to S1P at any concentration, S1P was suggested to be a chemotactic factor that is specific for Muse cells.

(3) Cell Kinetics Analysis Technology (TAXIScan Technology)

Figure 4:
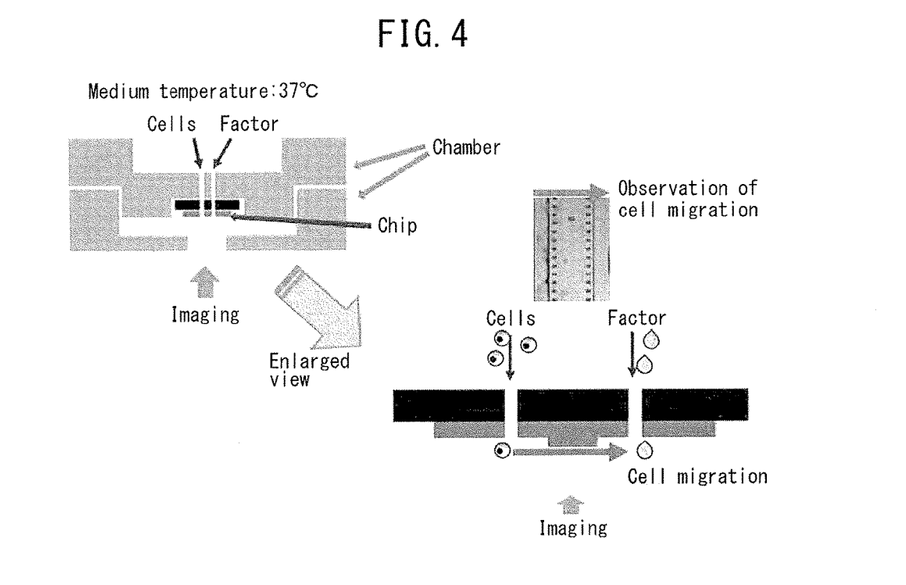
FIG. 4 is a conceptual drawing of a basic cell kinetics analysis apparatus (EZ-TAXIScan) used to measure migration of Muse cells. The apparatus contains two slits, cells and chemotactic factor are respectively added to each slit, and the manner in which the cells orient towards the chemotactic factor on the plate is indicated with arrows.
Figure 5:
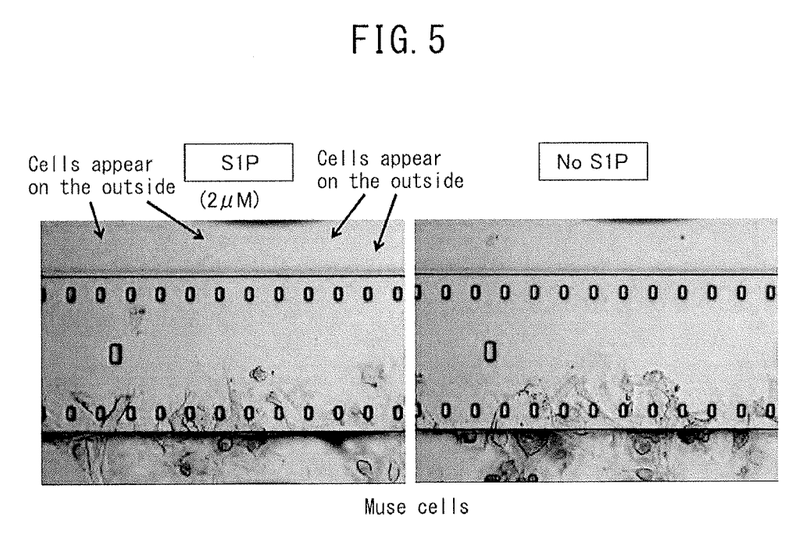
FIG. 5 depicts photographs showing cell migration measured using a basic cell kinetics analysis apparatus. Muse cells migrate by following the concentration gradient of a chemotactic factor so as to pass under a structure referred to as a terrace having a length of 250 mm and depth of 8 µm. The photograph on the left shows cell kinetics in the case of the addition of sphingosine-1-phosphate (S1P) at a concentration of 2 µM, while the photograph on the right shows cell kinetics in the case of not adding S1P.

Cell kinetics analysis technology is a technology for analyzing cell chemotactic activity developed by ECI Inc. (see Nitta, et al., Journal of Immunological Methods, 320, 155-163 (2007)). In an apparatus using this analytical method, a system is used that enables measurement of chemotactic activity of cells dependent on a concentration gradient in the horizontal direction by forming a constant concentration gradient of a chemotactic factor using a silicon wafer chip fabricated using the latest microfabrication technology (FIG. 4). Directivity (such as the degree to which Muse cells proceed towards the high concentration side of a chemotactic factor in a certain direction) can be quantified by analyzing the results obtained from this system in the form of images (FIG. 5).

Figure 6:
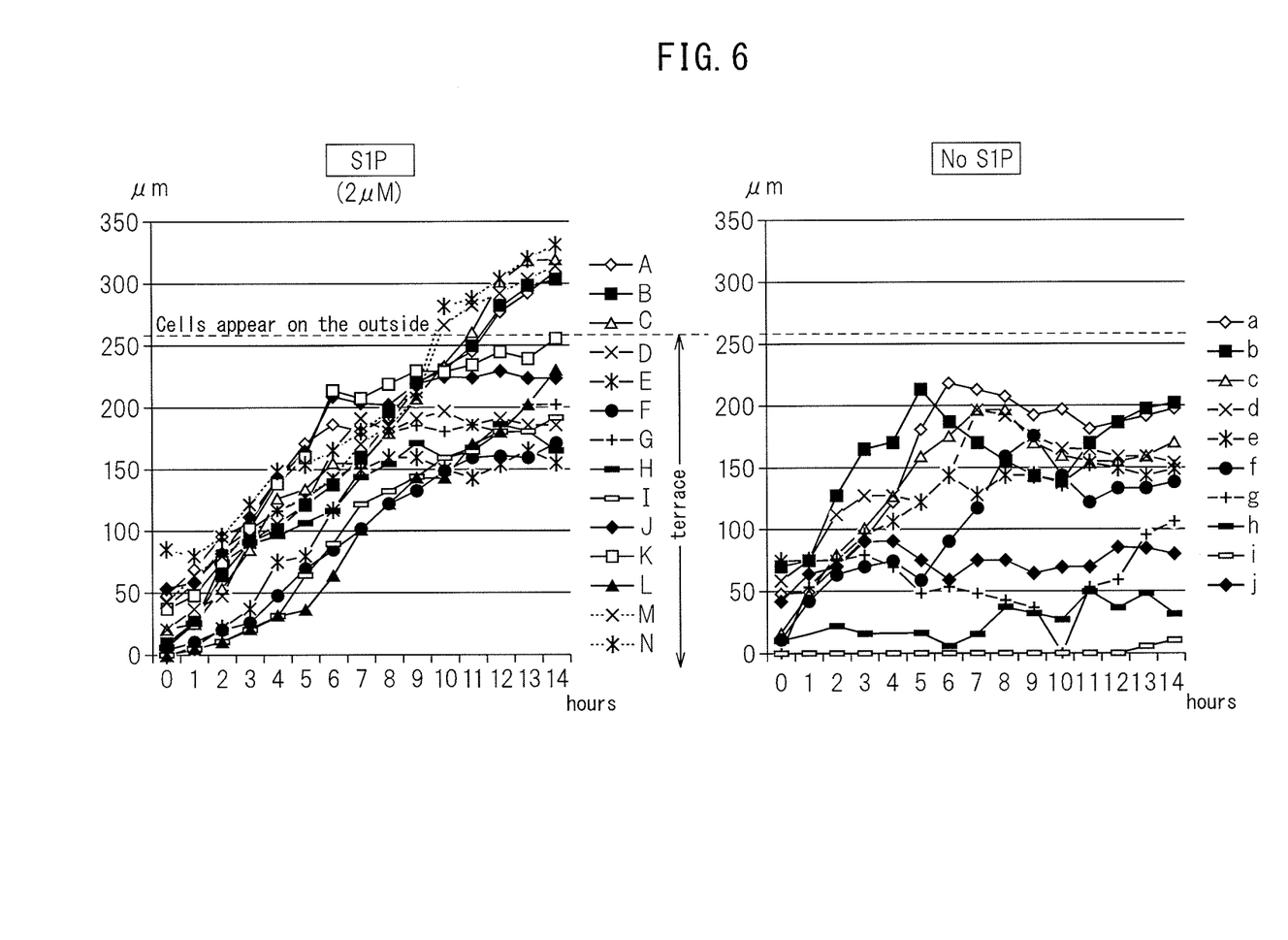
FIG. 6 indicates the results of analyzing migration of Muse cells induced by S1P using a basic cell kinetics analysis apparatus. The graph on the left indicates the results of real-time measurement of the manner in which Muse cells migrate linearly towards S1P. The graph on the right indicates the results of real-time measurement of the manner in which Muse cells spread out randomly in the absence of S1P.

More specifically, Muse cells were added to one of the slits having a diameter of about 1 mm provided in a chamber above the chip at an arbitrary density, while chemotactic factor in the form of S1P was added from the other slit. Time-lapse photography was started following the addition of the cells and S1P and observations were made for about 14 hours. Cell chemotactic activity was evaluated by measuring the distance each of the cells migrated in the direction of length over a terrace provided on the silicon wafer chip having a structure measuring 1200 μm wide, 250 μm long and about 8 μm deep. Furthermore, a system to which S1P was not added was used as a control. The graph on the left side of FIG. 6 shows the results of observing the chemotactic activity of Muse cells (A to N) on a real-time basis in the case of having added S1P at a concentration of 2 μM. The graph on the right side of FIG. 6 shows the results of observing the movement of Muse cells in the case of having not added S1P. In the system in which S1P was added, the Muse cells (A to N) were determined to pass linearly through the terrace while following the concentration gradient of S1P. In addition, although some cells were unable to pass through the terrace, this is thought to have been mainly caused by the presence of columns provided in the terrace having obstructed migration of cells (right side of FIG. 6). On the other hand, in the system in which S1P was not added, Muse cells (a to j) were observed to only spread out randomly (left side of FIG. 6). On the basis of the above results, S1P was strongly suggested to be a chemotactic factor specific to Muse cells in the same manner as in the case of having evaluated chemotactic activity using a Boyden chamber.

In addition, the chemotactic activity of Muse cells was observed on a real-time basis in the same manner as described above using an S1PR2 agonist in the form of 1-(2-(1-benzyl-2,5-dimethyl-1H-pyrrol-3-yl)-2-oxoethyl)-5-(trifluoromethyl) pyridin-2(1H)-one instead of S1P (data not shown). In a system in which this agonist was added (2 μM), a state was observed in which Muse cells passed linearly through the terrace while following the concentration gradient of the agonist. On the base of the above results, this agonist was confirmed to demonstrate chemotactic activity with respect to Muse cells.

(4) Accumulation of Muse Cells by Chemotactic Factor In Vivo

Figure 7:
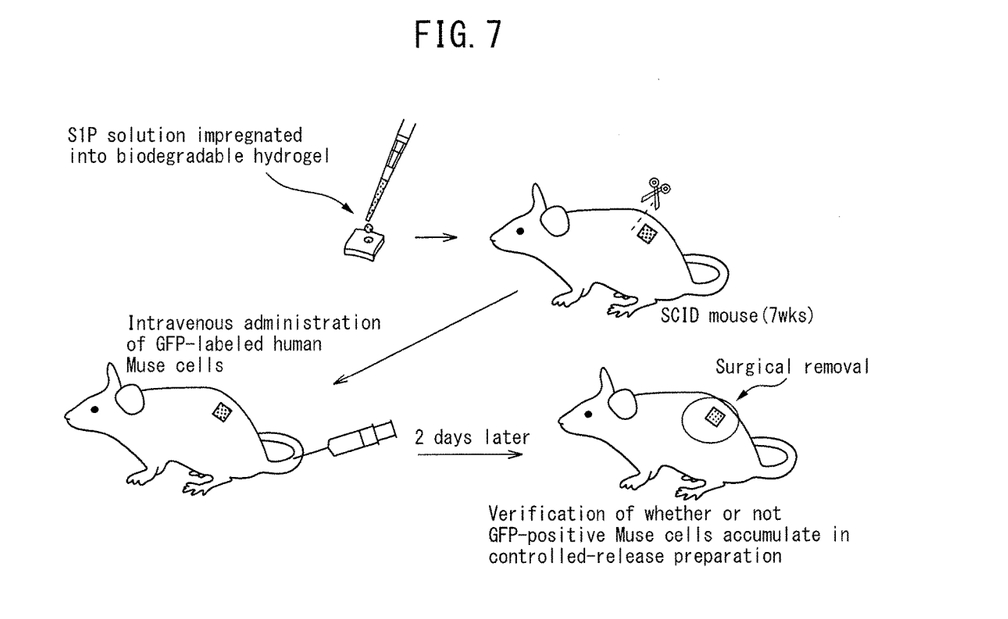
FIG. 7 is a drawing for explaining the procedure of a migration test of Muse cells in mice using a chemotactic factor. The mice consisted of immunodeficient SCID mice (age 7 weeks) that do not reject human cells. A biodegradable hydrogel impregnated with an S1P solution was transplanted onto the backs of the mice, and after administering GFP-positive human Muse cells into a tail vein, tissue was collected from the vicinity of the hydrogel transplant site to verify whether or not Muse cells had accumulated at the site.

Whether or not Muse cells are accumulated by a chemotactic factor in the body was determined in the manner described below using mice for the experimental model (see FIG. 7). The mice used were immunodeficient SCID mice that do not reject human cells (males, age 7 weeks) purchased from Japan SLC, Inc. or Charles River Laboratories Japan, Inc. S1P was used for the chemotactic factor. Biodegradable hydrogel (MedGel™) measuring 0.5 cm×0.5 cm preliminarily impregnated with an S1P solution (500 nM or 1,000 nM) was transplanted to an arbitrary site on the backs of the mice. Subsequently, GFP-labeled human Muse cells prepared in Example 1 were injected into a tail vein of the mice. Two days later, tissue in the vicinity of the hydrogel was removed from the transplanted site, the GFP label was detected using GFP antibody, and the number of GFP-positive Muse cells was counted with a laser scanning microscope.

Figure 8:
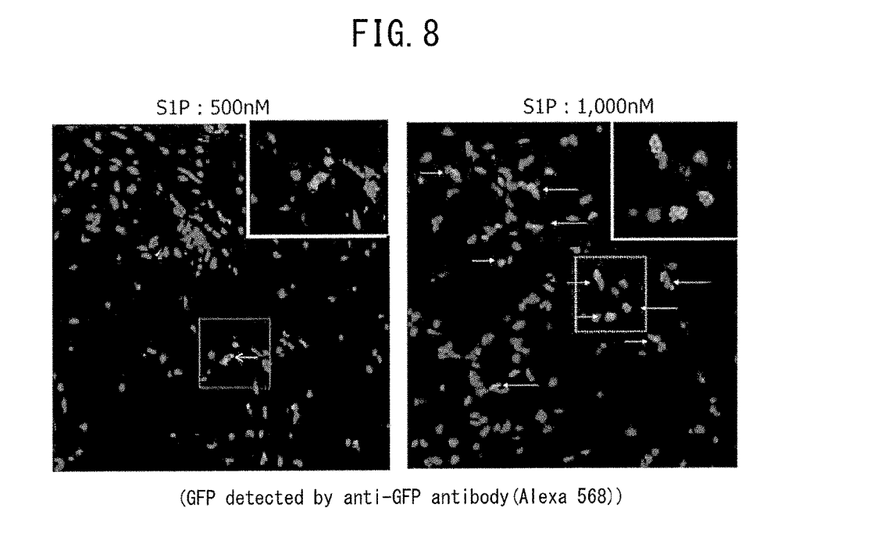
FIG. 8 depicts drawings showing the accumulation of GFP-positive human Muse cells that accumulated in hydrogel in the case of making the concentration of S1P solution 500 nM or 1,000 nM. Anti-GFP antibody (Alexa 568) was used to stain the GFP. These results indicate that Muse cells are accumulated dependent on the concentration of the S1P solution.

More specifically, the removed hydrogel was stained according to commonly used histochemical techniques using anti-GFP antibody to GFP (Alexa 568, purchased from Invitrogen). The stained images are shown in FIG. 8.

Figure 9:
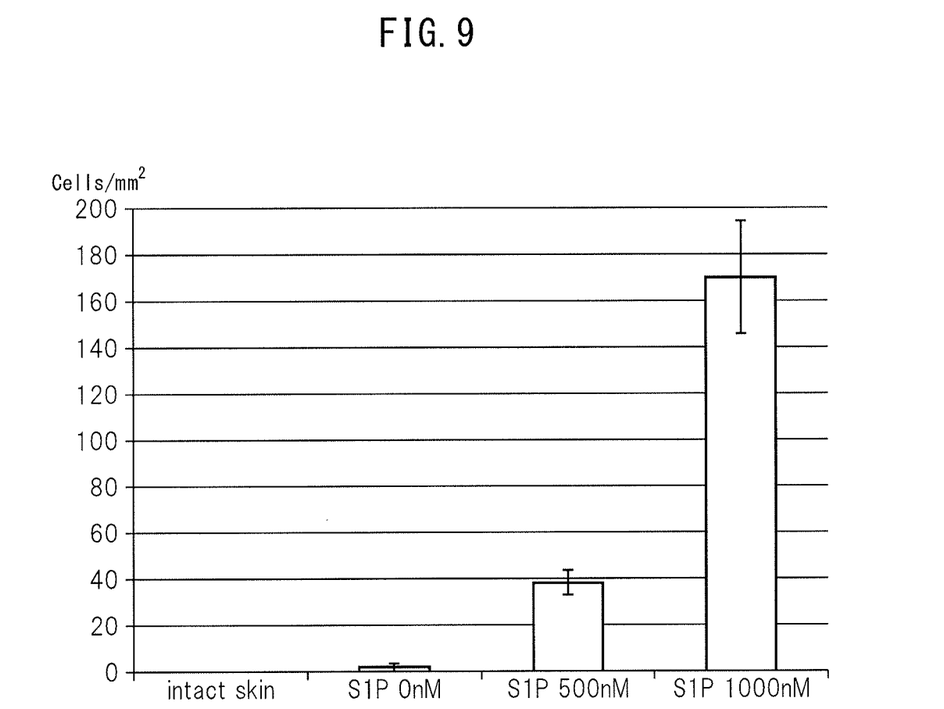
FIG. 9 shows the results of evaluating the number of Muse cells that accumulated in hydrogel as the number of cells per square millimeter (1 $mm^2$). Similar to the results shown in FIG. 8, the Muse cells were accumulated dependent on the concentration of the S1P solution.

Portions indicated by arrows indicate GFP-positive Muse cells. When a comparison is made between the case of an S1P concentration of 500 nM (left side of FIG. 8) and the case of an S1P concentration 1,000 nM (right side of FIG. 8), the number of Muse cells can be seen to increase dependent on the concentration of S1P. In the drawings, the enlarged upper right images are enlarged images of the framed portions in the center. In addition, the results of counting the number of cells based on each of the resulting images are shown in FIG. 9. On the basis of these results as well, Muse cells were determined to be accumulated dependent on the concentration of S1P.

INDUSTRIAL APPLICABILITY

The pharmaceutical composition of the present invention is able to provide a novel medical application used for the purpose of efficient tissue regeneration in regenerative medicine using Muse cells by enabling Muse cells to accumulate at a damaged site.

All publications and patent documents cited in the present description are incorporated in the present description in their entirety by reference. Furthermore, although specific embodiments of the present invention have been explained in the present description for the purpose of indicating examples, it should be understood by a person with ordinary skill in the art that various modifications may be made to the present invention without deviating from the spirit and scope thereof.

The invention claimed is:

1. A method for activating migration of pluripotent stem cells, the method comprising: administering a compound to a subject that activates sphingosine-1-phosphate receptor 2 as an active ingredient thereof, wherein the compound is selected from the group consisting of 1-(2-(1-benzyl-2,5-dimethyl-1H-pyrrol-3-yl)-2-oxoethyl)-5-(trifluoromethyl) pyridin-2(1H)-one, 1-(2-(1-benzyl-2,5-dimethyl-1H-pyrrol-3-yl)-2-oxoethyl)-3-methylimidazolindine-2,4,5-trione, 1-(1-benzyl-2,5-dimethyl-1H-pyrrol-3-yl)-2-((1-methyl-1H-tetrazol-5-yl)thio)ethanone, and (S)-1-(2-(1-benzyl-2,5-dimethyl-1H-pyrrol-3-yl)-2-oxoethyl-2',3'-dihydrospiro [imidazolidine-4,1'-indene]-2,5-dione, to thereby activate migration of pluripotent stem cells.

2. The method according to claim 1, wherein the compound that activates sphingosine-1-phosphate receptor 2 is an agonist of sphingosine-1-phosphate receptor 2.

3. The method according to claim 1, wherein activation of migration is guidance to a damaged site in the body.

4. The method according to claim 1, wherein the pluripotent stem cells are SSEA3-positive.

5. The method according to claim 1, wherein the pluripotent stem cells are CD105-positive.

6. The method according to claim 1, wherein the pluripotent stem cells are CD117-negative and CD146-negative.

7. The method according to claim 1, wherein the pluripotent stem cells are CD117-negative, CD146-negative, NG2-negative, CD34-negative, vWF-negative and CD271-negative.

8. The method according to claim 1, wherein the pluripotent stem cells are CD34-negative, CD117-negative, CD146-negative, CD271-negative, NG2-negative, vWF-negative, Sox10-negative, Snail-negative, Slug-negative, Tyrp1-negative and Dct-negative.

9. The method according to claim 1, wherein the pluripotent stem cells are pluripotent stem cells having all of the following properties:
 (i) low or absent telomerase activity;
 (ii) ability to differentiate into cells of any of the three germ layers;
 (iii) absence of demonstration of neoplastic proliferation; and,
 (iv) presence of self-renewal ability.

10. The method according to claim 1, wherein the compound is formulated as a pharmaceutical composition.

11. The method according to claim 10, wherein the pharmaceutical composition is a member selected from the group consisting of an injection preparation, an oral preparation, a suppository, and an inhalant.

12. The method according to claim 10, wherein the pharmaceutical composition is administered directly into a damaged site.

* * * * *

UNITED STATES PATENT AND TRADEMARK OFFICE
CERTIFICATE OF CORRECTION

PATENT NO. : 10,034,889 B2
APPLICATION NO. : 15/238020
DATED : July 31, 2018
INVENTOR(S) : Mari Dezawa et al.

Page 1 of 1

It is certified that error appears in the above-identified patent and that said Letters Patent is hereby corrected as shown below:

On the Title Page

Under the "Related U.S. Application Data" heading, item (66), please delete "14/711,588" and insert --14/771,588--.

In the Specification

In Column 5, Line 23: please delete "antibody" and insert --an antibody--.

In Column 11, Line 61: after "purpose" please insert --of--.

In Column 15, Line 33: please delete "base" and insert --basis--.

Signed and Sealed this
Twenty-fifth Day of December, 2018

Andrei Iancu
*Director of the United States Patent and Trademark Office*